(12) United States Patent  (10) Patent No.: US 7,477,726 B2
Kabumoto  (45) Date of Patent: Jan. 13, 2009

(54) X-RAY INSPECTION APPARATUS

(75) Inventor: Takashi Kabumoto, Ritto (JP)

(73) Assignee: Ishida Co., Ltd., Kyoto (JP)

( * ) Notice: Subject to any disclaimer, the term of this patent is extended or adjusted under 35 U.S.C. 154(b) by 130 days.

(21) Appl. No.: 11/570,237

(22) PCT Filed: Mar. 25, 2005

(86) PCT No.: PCT/JP2005/005536

§ 371 (c)(1),
(2), (4) Date: Dec. 8, 2006

(87) PCT Pub. No.: WO2005/121757

PCT Pub. Date: Dec. 22, 2005

(65) Prior Publication Data

US 2008/0063148 A1 Mar. 13, 2008

(30) Foreign Application Priority Data

Jun. 11, 2004 (JP) ............................. 2004-173829

(51) Int. Cl.
G01N 23/04 (2006.01)
A61B 6/08 (2006.01)
(52) U.S. Cl. ........................................ 378/57; 378/205
(58) Field of Classification Search ................... 378/20, 378/64, 68, 69, 203, 205, 57, 208, 209
See application file for complete search history.

(56) References Cited

U.S. PATENT DOCUMENTS 3,974,388 A * 8/1976 Distler et al. ................. 378/20
5,029,192 A * 7/1991 Schwierz ........................ 378/4
2002/0186819 A1* 12/2002 Proksa ........................ 378/207
2004/0057557 A1* 3/2004 Nafstadius .................. 378/209

FOREIGN PATENT DOCUMENTS

JP 2002-71588 A 3/2002
JP 2003-50216 A 2/2003
JP 2003225236 A * 8/2003
JP 2003-279500 A 10/2003

* cited by examiner

Primary Examiner—Edward J Glick
Assistant Examiner—Mona M Sanei
(74) Attorney, Agent, or Firm—Global Ip Counselors, LLP

(57) ABSTRACT

The present invention provides an X-ray inspection apparatus with a simple constitution that can easily verify whether a transport conveyor is properly mounted without the need for a separate component to perform such verification. With the X-ray inspection apparatus, the shield units, which each block a portion of X-rays irradiated from the X-ray irradiating device, are provided to the conveyor. These shield units are constituted so that the X-rays detected by some of the pixels, which constitute the X-ray line sensor, are less than that at other pixels. The control computer stores the position, number, and the like of the pixels in which the amount of X-rays detected is reduced when the conveyor is properly mounted, and, before starting the inspection for foreign matter contamination, determines whether there is a mount failure of the conveyor by irradiating a small amount of X-rays and detecting whether X-rays are detected at the pixels that were stored.

8 Claims, 9 Drawing Sheets

X-RAY INSPECTION APPARATUS

FIELD OF THE INVENTION

The present invention relates to an X-ray inspection apparatus that inspects a product for foreign matter contamination and the like by irradiating the product with X-rays while being transported.

BACKGROUND OF THE INVENTION

On a conventional production line for products, such as foodstuffs, an X-ray inspection apparatus is used to inspect for defective products in order to prevent the shipment of such products, such as those that are cracked or contaminated with foreign matter. With this X-ray inspection apparatus, products to be inspected are irradiated with X-rays while being continuously transported by a transport conveyor. The transmittance state of those X-rays is detected by an X-ray receiving unit, and a determination is made as to whether each inspected product is contaminated with foreign matter, whether it has cracks, whether there is a shortage in the number of items it contains, and the like. In addition, there are also cases in which the X-ray inspection apparatus performs an inspection that counts the number of the items in the product to be inspected.

In such an X-ray inspection apparatus, if the inspection target is a product like a foodstuff, then the transport conveyor is repeatedly dismounted and cleaned in order to maintain sanitary conditions. If the transport conveyor, which is repeatedly mounted and dismounted any number of times, is not mounted at the normal position when remounted, then there is a risk that the X-rays will scatter inside the apparatus and leak to the outside of the apparatus if the X-rays are irradiated with the transport conveyor in this state.

Consequently, an X-ray inspection apparatus has been proposed (refer to Patent Document 1) that is provided with a function for verifying whether the transport conveyor, which transports the products to be inspected, is properly mounted. With the X-ray inspection apparatus disclosed in Japanese Published Unexamined Patent Application No. 2002-71588 (published on Mar. 8, 2002), an open state detecting device is disposed at the mount position of the transport conveyor inside the apparatus, and if the transport conveyor is not properly mounted, then the open state detecting device detects the unshielded state and prohibits the irradiation of X-rays. Thereby, the leakage of X-rays to the outside of the apparatus is prevented when the X-rays are irradiated in the state wherein the transport conveyor is not properly mounted, as well as in the state wherein the mounting of the transport conveyor has been neglected.

DISCLOSURE OF THE INVENTION

Nevertheless, the abovementioned conventional X-ray inspection apparatus has problems, as described below.

Namely, the X-ray inspection apparatus disclosed in the abovementioned publication provides an open state detection device that detects the mount state of the transport conveyor, and it is consequently possible to easily verify whether the transport conveyor is properly mounted and thereby prevent the leakage of X-rays; nevertheless, there is a problem in that the need for a separate open-state detecting device will lead to an increase in costs.

It is an object of the present invention to provide an X-ray inspection apparatus with a simple constitution that can easily verify whether a transport unit is properly mounted without the need for a separate component to perform such verification.

An X-ray inspection apparatus according to a first aspect is an X-ray inspection apparatus that inspects a product, which is being transported, by irradiating the product with X-rays and detecting the X-rays that pass through the product, comprising an irradiation unit, a light receiving unit, a transport unit, an X-ray shield unit, and a control unit. The irradiation unit irradiates the product to be inspected with X-rays. The light receiving unit detects the X-rays irradiated from the irradiation unit. The transport unit, which is disposed between the irradiation unit and the light receiving unit, transports the product to be inspected. The X-ray shield unit is integral with the transport unit, blocks a portion of the X-rays irradiated from the irradiation unit, and is formed in the transport unit in an area irradiated by the X-rays. The control unit detects the position at which the X-rays are blocked by the X-ray shield unit based on the amount of X-rays detected at the light receiving unit. Further, the control unit determines whether the transport unit is properly mounted based on the position.

Here, the X-ray shield unit, which blocks the X-rays irradiated from the irradiation unit, is formed integrally with the transport unit, which transports the product to be inspected. Further, before starting the inspection of the products, X-rays are irradiated from the irradiation unit and the position at which the X-rays are blocked by the abovementioned X-ray shield unit is detected at the light receiving unit, which detects the X-rays that pass through the product. If the position of the area wherein the amount of X-rays detected at the light receiving unit blocked by the X-ray shield unit is less than that of another area matches the position that should be detected if the transport unit is properly mounted, then the control unit determines that the transport unit is properly mounted. However, if the position of the area, wherein the amount of X-rays detected at the light receiving unit blocked by the X-ray shield unit is small, deviates from the position that should be detected if the transport unit is properly mounted, or if the area, wherein the amount of X-rays detected is small, cannot be detected, then the control unit determines that the transport unit is not properly mounted.

Here, if the transport unit, which transports the product to be inspected, is not properly mounted to the main body of the X-ray inspection apparatus, then there is a risk that the X-rays that scatter inside the apparatus will leak to the outside of the apparatus. Consequently, even with a conventional X-ray inspection apparatus, a switch and the like that permits the irradiation of X-rays based on the proper mounting of the transport unit is provided as a means to detect whether the transport unit is properly mounted to the main body of the X-ray inspection apparatus prior to starting the inspection of the product. However, there is a problem with the method that uses such a switch in that it increases costs and is troublesome to manufacture.

Accordingly, with the X-ray inspection apparatus of the present invention, the X-ray shield unit, which is integral with the transport unit, is formed in order to verify the proper mounting of the transport unit. Thereby, it is possible to easily verify whether the transport unit is properly mounted by detecting the portion at which the X-rays are blocked by the X-ray shield unit at the light receiving unit, i.e., the portion wherein the amount of X-rays detected is small, and comparing such with the position that should be detected if the transport unit is properly mounted. Thereby, it is possible to verify whether the transport unit is properly mounted by a simple constitution wherein an X-ray shield unit is formed in the transport unit, without separately providing a complicated mechanism, such as a switch.

Furthermore, the X-ray shield unit may be integrated with the transport unit by forming the X-ray shield unit integrally as part of the transport unit, or by forming the X-ray shield unit separately and independently and then integrating it with the transport unit by fixing it thereto.

An X-ray inspection apparatus according to a second aspect is an X-ray inspection apparatus according to the first aspect, wherein the control unit prohibits the irradiation of X-rays from the irradiation unit if it is determined that the transport unit is not properly mounted.

Here, if the control unit determines that the transport unit is not properly mounted by irradiating the X-rays before starting the inspection of the product, then the control unit performs control so as to prohibit the irradiation of X-rays from the irradiation unit.

Thereby, even if the transport unit is not properly mounted, it is possible to avoid the risk of X-rays scattering inside the apparatus and leaking to the outside of the apparatus.

An X-ray inspection apparatus according to a third aspect is an X-ray inspection apparatus according to the first aspect or the second aspect, further comprising a storage unit that stores the position of the light receiving unit at which the X-rays are blocked by the X-ray shield unit when the transport unit is properly mounted.

Here, the position of the light receiving unit wherein the X-rays are blocked by the X-ray shield unit when the transport unit is mounted at the normal position, i.e., the portion where the amount of X-rays detected at the light receiving unit is less than that at another area, is stored.

Thereby, it is possible to easily verify whether the transport unit is properly mounted by irradiating X-rays prior to starting the inspection of the product and determining whether the position of the portion, wherein the amount of the abovementioned X-rays detected at the light receiving unit is small, matches the position stored in the storage unit. For example, if the position stored in the storage unit does not match the actual detection result, then it is determined that the mounting of the transport unit is not proper. Furthermore, if the position stored in the storage unit matches the actual detection result, then it can be determined that the mounting of the transport unit is proper. As a result, it is possible to easily determine whether the transport unit is properly mounted, and it is also possible to reliably avoid a situation wherein the product is inspected by irradiating X-rays in a state wherein the mounting of the transport unit is inadequate.

An X-ray inspection apparatus according to a fourth aspect is an X-ray inspection apparatus according to any one of the first through third aspects, wherein the X-ray shield unit is formed integrally with a frame that constitutes the transport unit.

Here, the X-ray shield unit is formed integrally with the frame that constitutes the transport unit, for example, like a slit or an opening formed in the frame of the transport unit.

Thereby, because the transport unit and the X-ray shield unit are formed integrally from the start, without having to integrate them, the constitution can be simplified compared with the case wherein the X-ray shield unit and the transport unit are separately formed.

An X-ray inspection apparatus according to a fifth aspect is an X-ray inspection apparatus according to any one of the first through fourth aspects, wherein the transport unit is a transport conveyor that comprises an endless transport belt that transports the product; a drive mechanism that rotates the transport belt; and the frame disposed on the inner side of the transport belt.

Here, a transport conveyor, which comprises a transport belt, a drive mechanism, and a frame, is used as the transport unit.

Thereby, it is possible to form the X-ray shield unit by using a portion of the frame, e.g., by using the opening, the slit, and the like formed in the frame.

An X-ray inspection apparatus according to a sixth aspect is an X-ray inspection apparatus according to the fifth aspect, wherein the X-ray shield unit is a portion of the frame that forms a slit that is formed in the frame provided by the transport conveyor.

Here, a slit is formed in the frame of the transport conveyor and the portion of the frame that forms this slit is used as the X-ray shield unit.

Thereby, because the X-rays are blocked by the portion of the frame that forms the slit that is formed in the frame of the transport conveyor, it is possible to easily verify whether the transport conveyor is properly mounted by setting the position of the blocked light receiving unit as a reference.

An X-ray inspection apparatus according to a seventh aspect is an X-ray inspection apparatus according to the fifth aspect, wherein the X-ray shield unit is a portion of the frame that forms an opening that is formed in the frame provided by the transport conveyor.

Here, the X-ray shield unit is formed as unit of the frame while taking into consideration the original positional relationship between the light receiving unit and the opening, which is formed in the frame of the transport conveyor, in order to detect the X-rays that pass through the product. In other words, the portion of the frame that forms the opening of the frame of the transport conveyor, which a conventional X-ray inspection apparatus also comprises, is used as the X-ray shield unit.

For example, part of the light receiving unit is disposed at a position where the X-rays are blocked by the portion of the frame that forms the opening. Thereby, when the transport conveyor is properly mounted, the amount of X-rays detected at the portion of the light receiving unit where the X-rays are blocked by the X-ray shield unit is less than that at another area; on the other hand, when the transport conveyor is not properly mounted, a large amount of X-rays are detected at the abovementioned portion of the light receiving unit.

Thus, it is possible to easily verify whether the transport unit is properly mounted based on whether X-rays are detected at the light receiving unit disposed at the position where the X-rays are blocked by the portion of the fame that forms the opening.

An X-ray inspection apparatus according to an eighth aspect is an X-ray inspection apparatus according to any one of the first through seventh aspects, wherein the light receiving unit is a line sensor.

Here, the line sensor is used as the light receiving unit. Furthermore, the line sensor is disposed, for example, in a direction perpendicular to the transport direction of the transport unit, and the X-rays are detected at each pixel of the line sensor. Here, when the transport unit is properly mounted and, for example, each end of the line sensor serves as an X-ray shield unit and the X-rays are blocked by the portions of the frame that form the opening that is formed in the frame, the detection of X-rays at a plurality of pixels on each end of the line sensor is examined.

Thereby, it is possible to easily verify whether the transport unit is properly mounted just by verifying whether X-rays are detected at prescribed pixels on each end of the line sensor.

An X-ray inspection apparatus according to a ninth aspect is an X-ray inspection apparatus according to the eighth aspect, wherein the X-ray shield unit is disposed at a position wherein the X-rays detected at one end or both ends of the line sensor are blocked.

Here, the X-ray shield unit is provided at a position that interferes with the detection of the X-rays, which are irradiated from the irradiation unit, at the end of the line sensor. For example, if the transport unit is a transport conveyor, then the line sensor should be longer than the length of the X-ray detection opening, which is formed in the frame, in the direction orthogonal to the transport direction.

By irradiating X-rays prior to inspecting the product, it is possible to determine that the transport unit is properly mounted if the position of the pixels, wherein the amount of X-rays detected is less than that at other pixels, matches a prescribed number of pixels from one end or each end of the line sensor. On the other hand, if the position of the pixels at which the amount of X-rays detected is small is shifted from the end of the line sensor, or is less than or greater than the prescribed number, or is not detected at all, then it can be determined that the transport unit is not properly mounted.

BEST MODE FOR CARRYING OUT THE INVENTION

An X-ray inspection apparatus according to one embodiment of the present invention will be described below with reference to FIG. 1 through FIG. 9B.

Overall Constitution of the X-ray Inspection Apparatus

Figure 1:
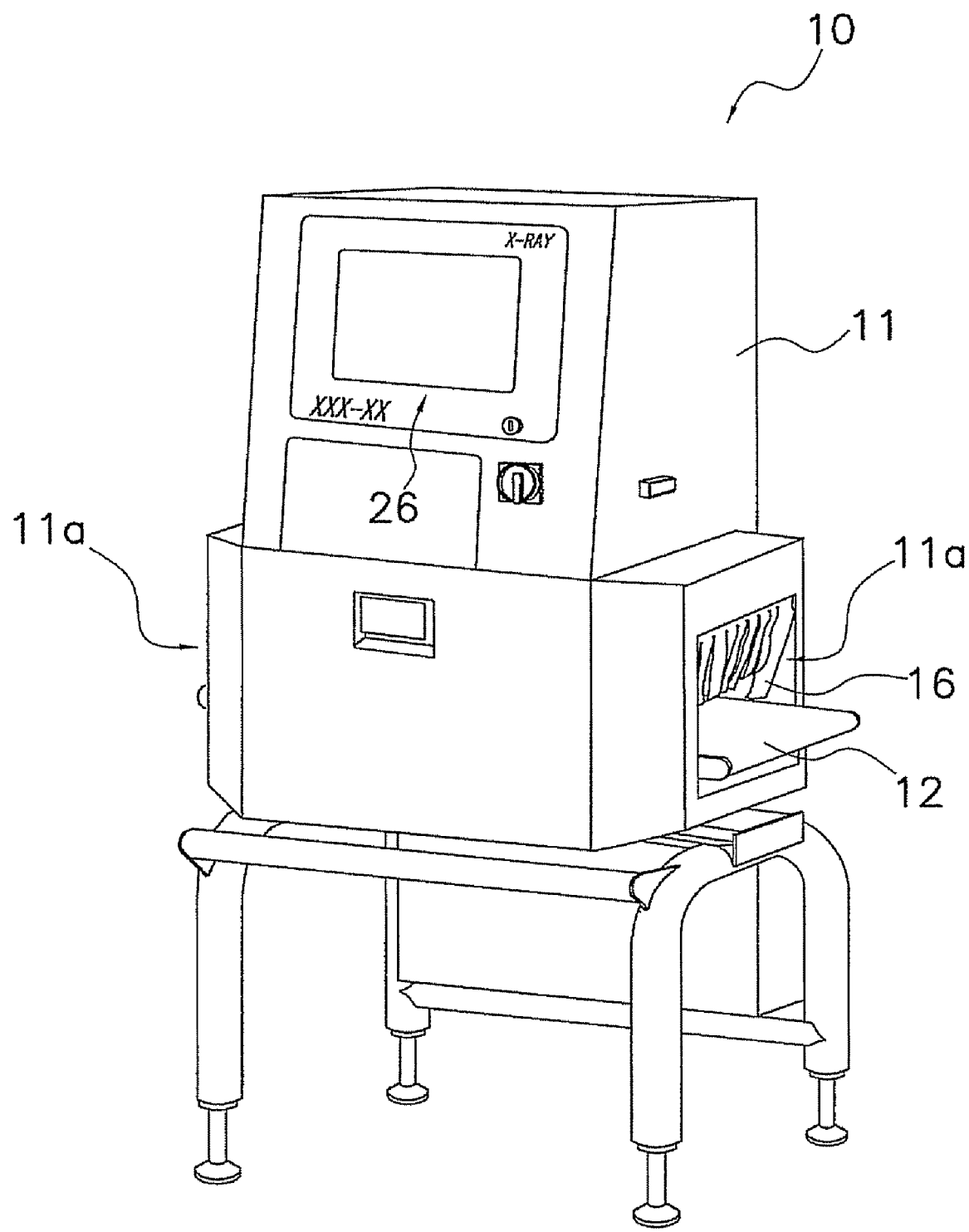
FIG. 1 is an external perspective view of an X-ray inspection apparatus according to one embodiment of the present invention.

As depicted in FIG. 1, an X-ray inspection apparatus 10 of the present embodiment is one of the apparatuses that performs a quality inspection on a production line for products like foodstuffs. The X-ray inspection apparatus 10 irradiates products, which are being continuously transported, with X-rays and performs an inspection to determine whether each product is contaminated with foreign matter, based on the amount of X-rays that transmit through the product.

Figure 2:
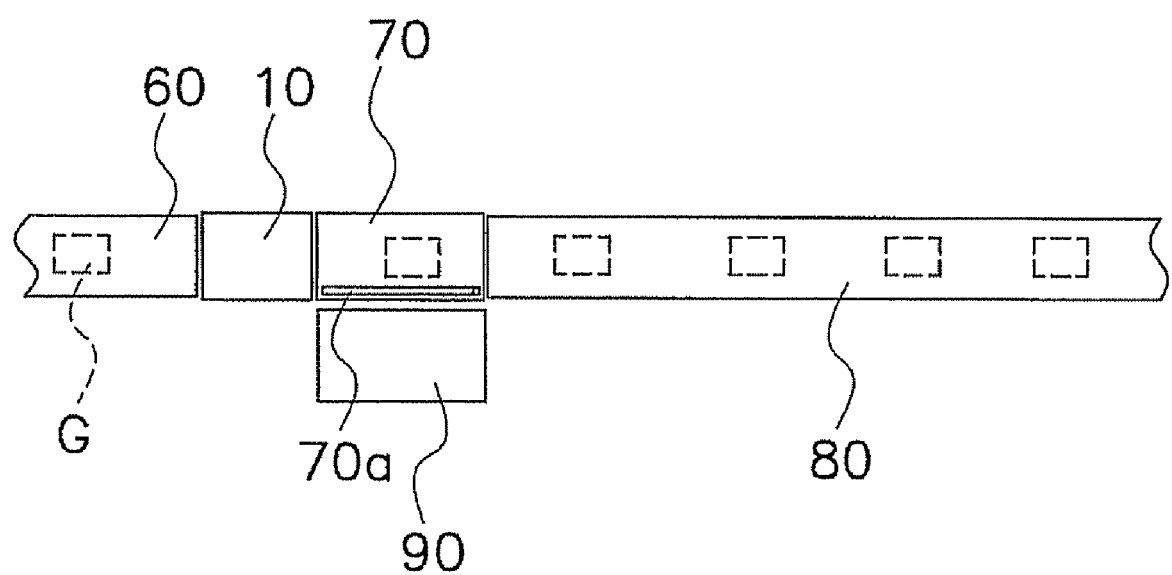
FIG. 2 depicts the constitution on the upstream and downstream sides of the X-ray inspection apparatus.

A product G, which is the product to be inspected by the X-ray inspection apparatus 10, is transported to the X-ray inspection apparatus 10 by an upstream conveyor 60, as depicted in FIG. 2. It is determined in the X-ray inspection apparatus 10 whether the product G has foreign matter contamination. The result of the determination by the X-ray inspection apparatus 10 is transmitted to a sorting mechanism 70, which is disposed on the downstream side of the X-ray inspection apparatus 10. If it is determined in the X-ray inspection apparatus 10 that the product G is a nondefective product, then the sorting mechanism 70 sends the product G, as is, to a line conveyor 80, which is the regular conveyor. On the other hand, if it is determined in the X-ray inspection apparatus 10 that the product G is a defective product, then an arm 70a, wherein a downstream side end thereof is a rotary shaft, swings so that it blocks the transport path. Thereby, the product G that was determined to be a defective product can be collected by a defective product collection box 90, which is disposed at a position spaced apart from the transport path.

Figure 3:
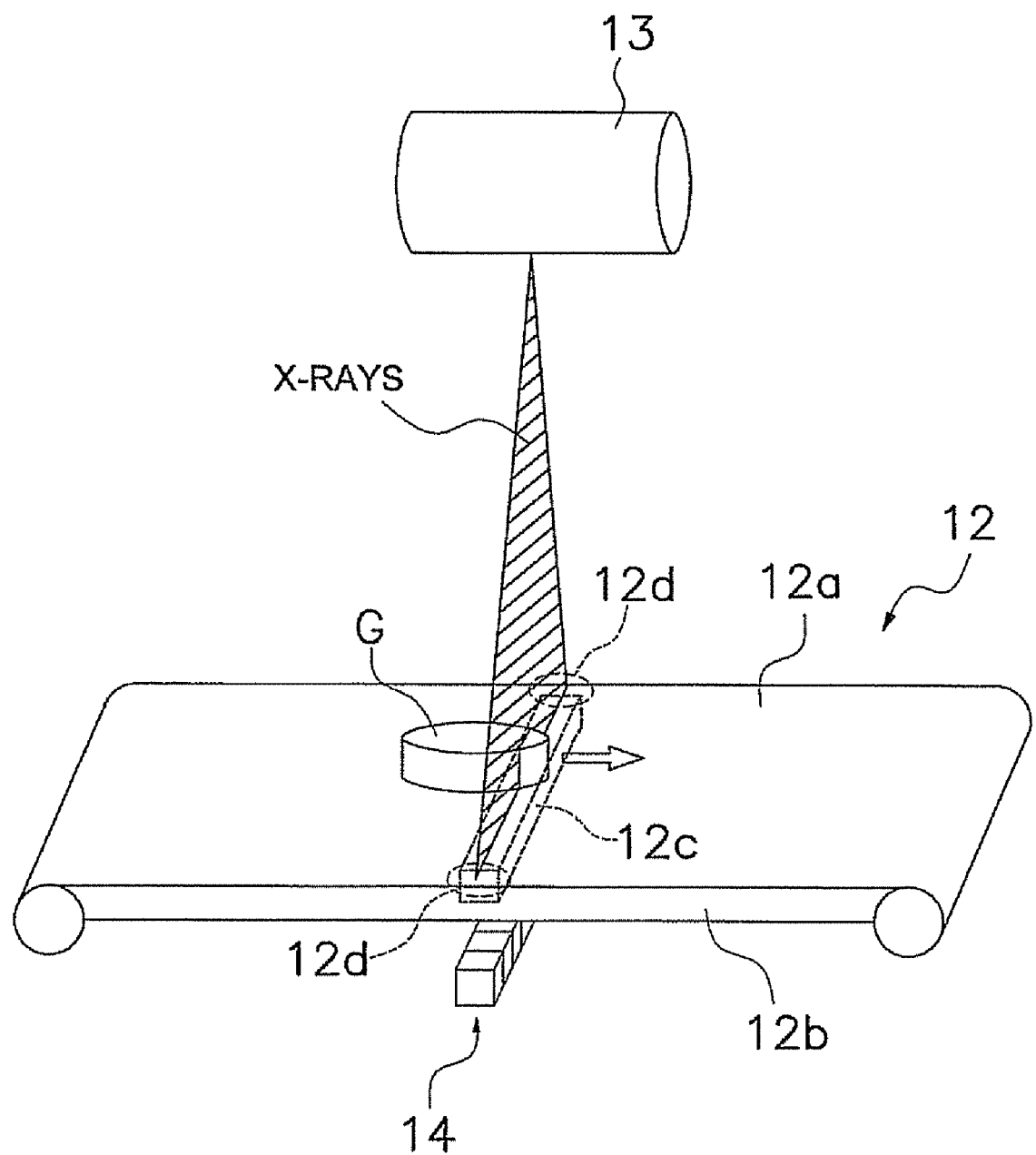
FIG. 3 is a simplified block diagram of the interior of a shield box of the X-ray inspection apparatus.

As depicted in FIG. 1, the X-ray inspection apparatus 10 principally comprises a shield box 11, a conveyor 12, shield curtains 16, and a monitor (display apparatus) 26 that includes a touch panel function. Furthermore, as depicted in FIG. 3, the interior of the X-ray inspection apparatus 10 comprises an X-ray irradiating device (irradiating unit) 13, an X-ray line sensor 14, and a control computer (control unit) 20 (refer to FIG. 6).

Shield Box

The shield box 11 has an opening 11a at the entrance side and the exit side surfaces of the shield box 11 in order to load and unload the product G The shield box 11 houses the conveyor 12, the X-ray irradiating device 13, the X-ray line sensor 14, the control computer 20, and the like.

In addition, as depicted in FIG. 1, each opening 11a is blocked by a shield curtain 16 in order to prevent the leakage of X-rays to the outside of the shield box 11. Each shield curtain 16 has a curtain unit, which is made of a lead containing rubber, and is pushed aside by the product when it is loaded and unloaded to and from the shield box 11.

In addition to a monitor 26, a key insertion slot, a power supply switch, and the like are disposed at the front upper part of the shield box 11.

Conveyor

Figure 6:
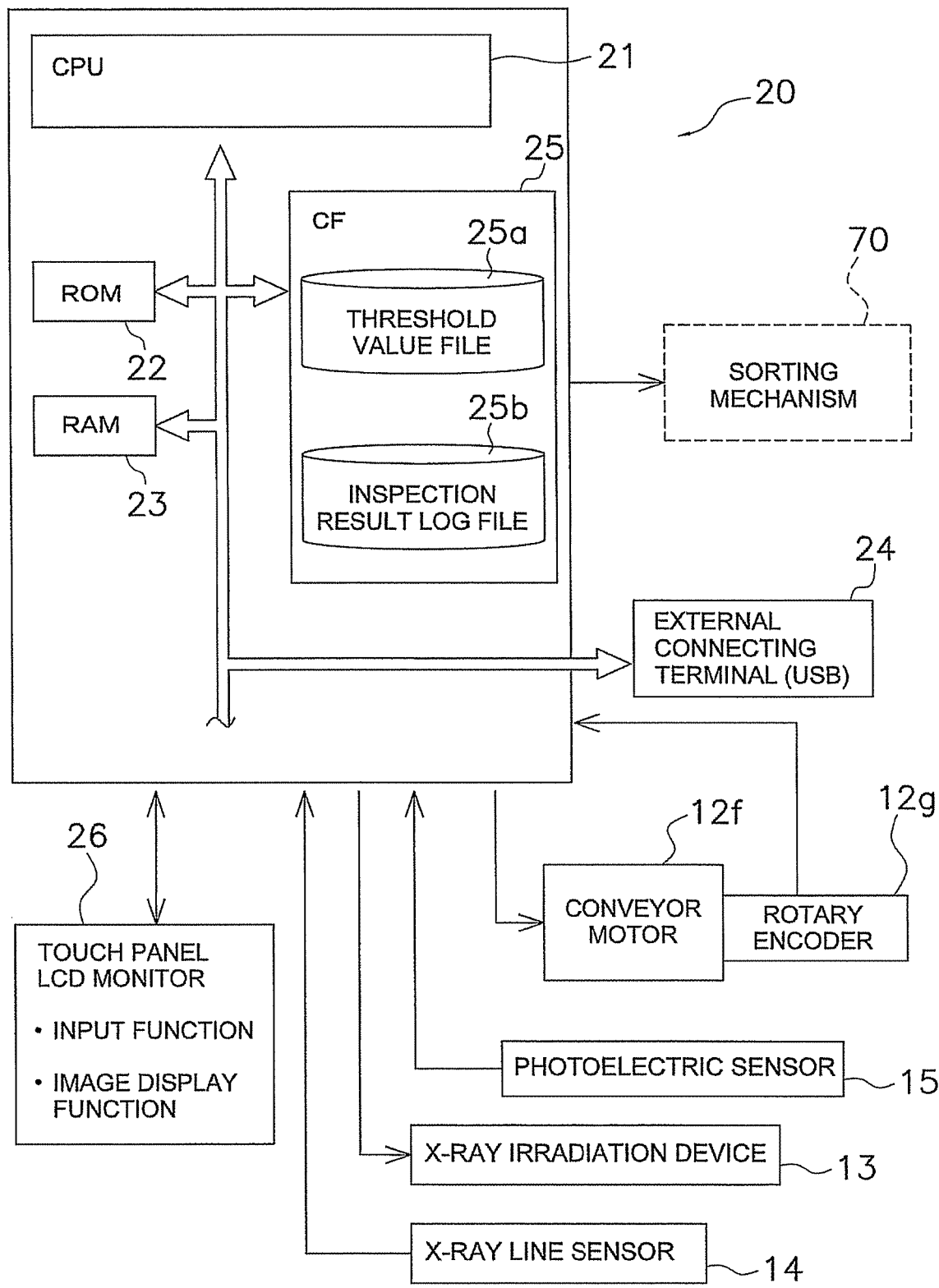
FIG. 6 is a block diagram of a control computer.
Figure 7:
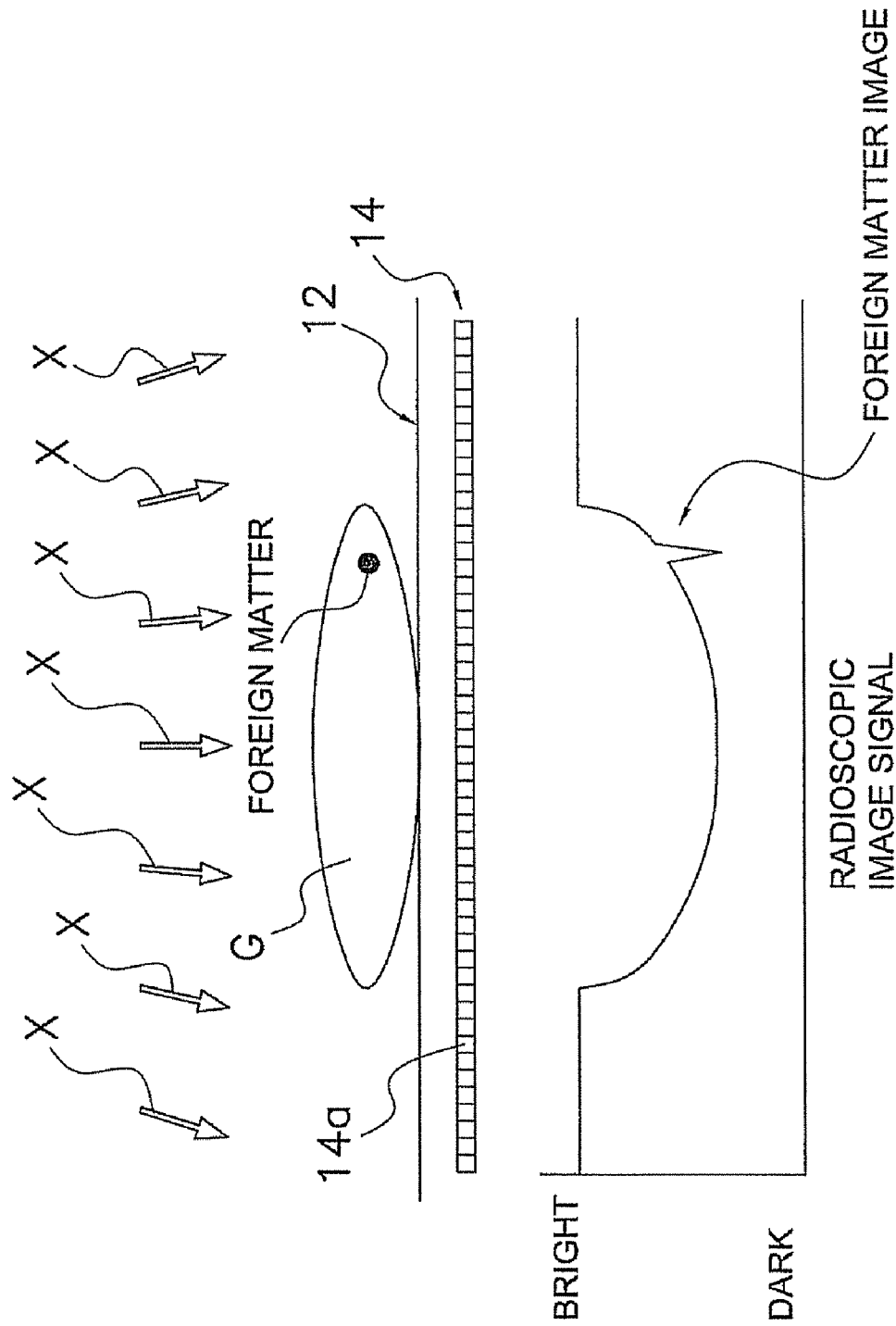
FIG. 7 is a schematic view that depicts the principle of X-ray inspection.

The conveyor 12 transports the product inside the shield box 11 and is driven by a conveyor motor (drive mechanism) 12f, which is included in a control block depicted in FIG. 6. The control computer 20 finely controls the transport speed of the conveyor 12 by means of inverter control of the conveyor motor 12f so that the transport speed is equal to the set speed that is input by a worker.

In addition, as depicted in FIG. 3, the conveyor 12 comprises a conveyor belt 12a and a conveyor frame 12b, and is removably attached to the shield box 11. Thereby, if inspecting foodstuffs and the like, then it is possible to frequently remove and clean the conveyor in order to maintain sanitary conditions inside the shield box 11.

The conveyor belt 12a is an endless belt and its inner side is supported by the conveyor frame 12b. Furthermore, the driving force of the conveyor motor 12f rotates the belt, which transports objects placed thereon in a prescribed direction.

Figure 4:
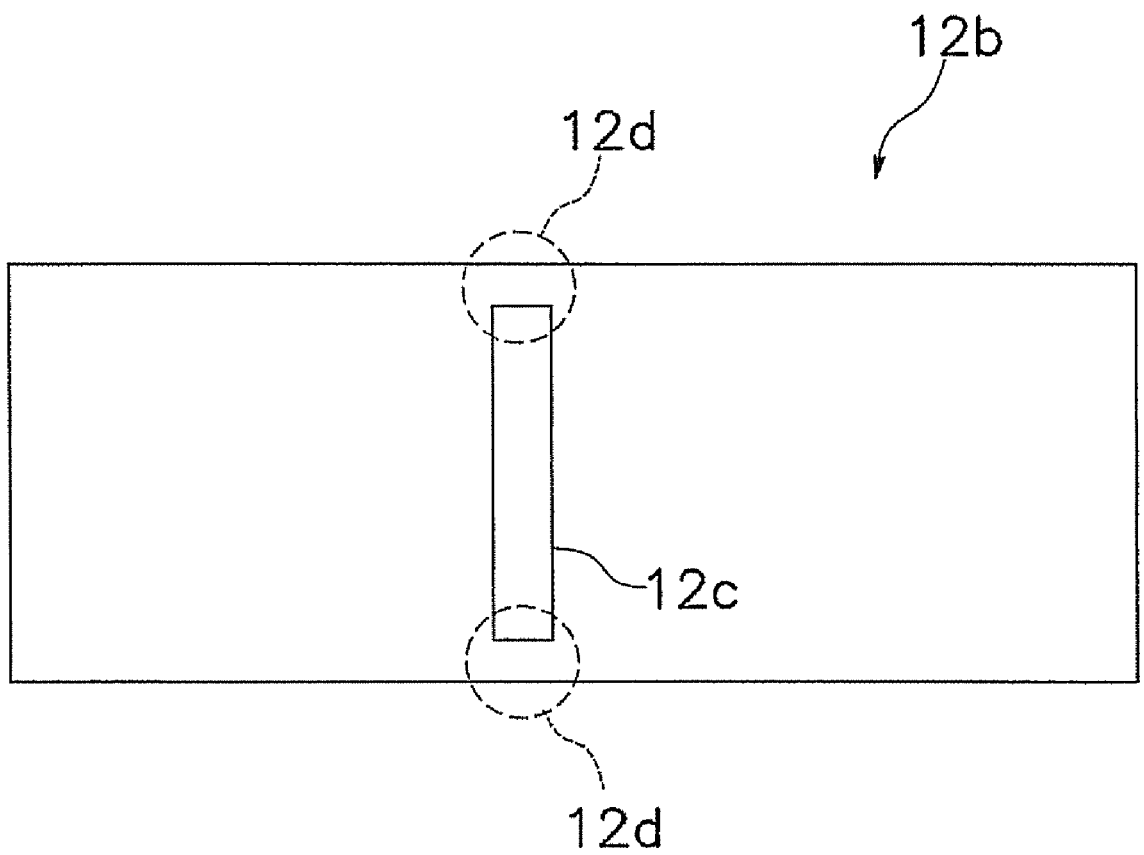
FIG. 4 is a plan view that depicts a conveyor frame inside the shield box of the X-ray inspection apparatus.

In addition to supporting the endless conveyor belt 12a from the inner side thereof, the conveyor frame 12b has an opening 12c, which is a long opening whose length is in a direction perpendicular to the transport direction, at a position opposing the surface of the inner side of the conveyor belt 12a, as depicted in FIG. 3 and FIG. 4. The opening 12c is formed in the conveyor frame 12b on a line that connects the X-ray irradiating device 13 and the X-ray line sensor 14. In other words, the opening 12c is formed in the conveyor frame 12b in an area irradiated by X-rays from the X-ray irradiating device 13 so that the conveyor frame 12b does not block the X-rays that transmit through the product G.

Figure 5A:
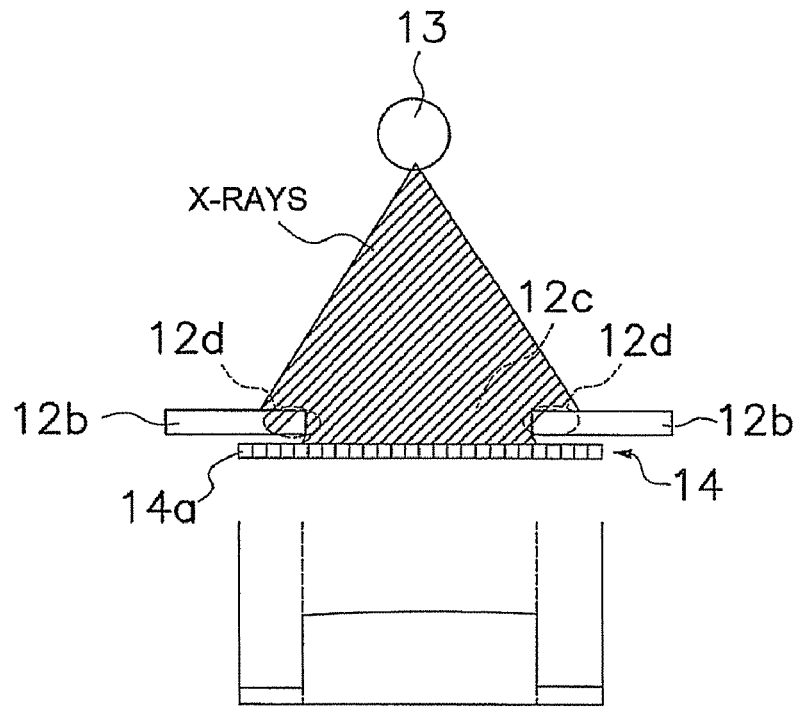
FIG. 5A depicts the X-ray irradiation state when the conveyor is mounted and a graph of the amount of X-rays detected by a line sensor at that time.

In addition, the forming of the opening 12c forms a shield unit (X-ray shield unit) 12d, which blocks some of the X-rays irradiated from the X-ray irradiating device 13, on each side of the opening 12c in the longitudinal direction as part of the conveyor frame 12b. As depicted in FIG. 3 and FIG. 5A, each shield unit 12d is a portion from an end of the opening 12c to an edge of the conveyor frame 12b in the direction orthogonal to the transport direction. Consequently, as depicted in FIG. 5A, a portion on each end of the X-rays that is radiated in a fan shape is blocked, which reduces the amount of X-rays detected at several pixels on each end of the X-ray line sensor 14, which is disposed below the conveyor 12. In addition, because the shield units 12d are formed as part of the conveyor 12, they are integral with the conveyor 12 and move integrally therewith.

X-ray Irradiating Device

As depicted in FIG. 3, the X-ray irradiating device 13 is disposed above the conveyor 12 and irradiates X-rays in a fan shape through the opening 12c, which is formed in the conveyor frame 12b, toward the X-ray line sensor (light receiving unit, line sensor) 14, which is disposed below the conveyor 12 (refer to the diagonally lined portion in FIG. 3).

Figure 5B:
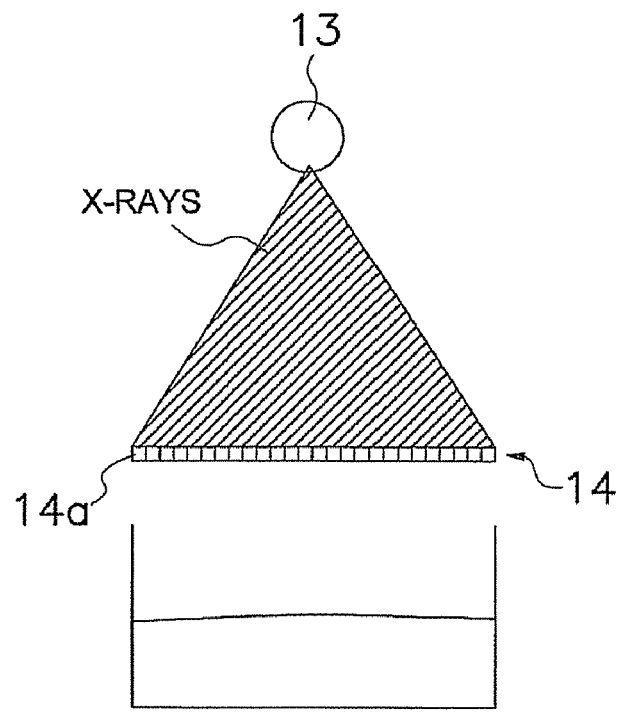
FIG. 5B depicts the X-ray irradiation state when the conveyor is unmounted and a graph of the amount of X-rays detected by the line sensor at that time.

Furthermore, as depicted in FIG. 3 and FIG. 5A, the X-rays irradiated from the X-ray irradiating device 13 are irradiated to an area that slightly protrudes (by several pixels of the X-ray line sensor 14) from each end of the opening 12c with respect to the center of the conveyor frame 12b, and, as depicted in FIG. 5B, to an area that includes pixels 14a on each end of the X-ray line sensor 14.

X-ray Line Sensor

The X-ray line sensor 14 is disposed below the conveyor 12 (the opening 12c and the shield unit 12d), and detects the X-rays that transmit through the product G, the conveyor belt 12a, and the like. As depicted in FIG. 5A, FIG. 5B, and the like, the X-ray line sensor 14 comprises a plurality of pixels 14a, which are horizontally disposed on a straight line oriented orthogonal to the transport direction of the conveyor 12.

Furthermore, FIG. 5A and FIG. 5B each depict the X-ray irradiation state inside the X-ray inspection apparatus 10 and a graph that indicates the amount of X-rays detected at that time at the pixels 14a that constitute the X-ray line sensor 14. The dashed lines in the graph drawn at the lower part of each of these graphs corresponds to the positions of the pixels 14a wherein the X-rays are blocked by the shield units 12d in the X-ray irradiation state drawn at the upper part (likewise for FIG. 9A and FIG. 9B).

Furthermore, if the conveyor 12 is attached at the prescribed position, then the X-rays are blocked from the X-ray line sensor 14 by the shield unit 12d on each end of the opening 12c, as graphed in FIG. 5A, and the amount of X-rays detected at several pixels (four to five pixels) at each end is less than at other pixels 14a. On the other hand, if the mounting of the conveyor 12 was neglected, then X-rays greater than the prescribed amount are detected at all pixels 14a, as graphed in FIG. 5B. Consequently, by detecting whether the amount of X-rays detected at prescribed pixels 14a (a plurality of pixels on each end) is less than at other pixels 14a, as depicted in the graph at the lower part of FIG. 5A, it is possible to detect whether the conveyor 12 is mounted, as well as to detect a mount failure and the like.

Monitor

The monitor 26 is a full dot display type liquid crystal display. In addition, the monitor 26 has a touch panel function and displays screens that prompt the input of parameters related to initial settings, failure determination, and the like.

In addition, the monitor 26 displays an X-ray image after image processing, which is discussed later, has been performed. This enables the user to visually perceive the presence, location, size, and the like of foreign matter contained in the product G Furthermore, the monitor 26 displays the conveyor 12 mount failure detection result, which is discussed later.

Control Computer

The control computer (control unit) 20 executes an image processing routine, an inspection determination processing routine, and the like included in a control program, in a CPU 21. In addition, the control computer 20 saves and accumulates, in a storage unit such as a CF (CompactFlash™) 25, the image that was used in the inspection for a defective product, the inspection result, the pixel information wherein the amount of X-rays detected when the conveyor 12 is mounted is less than that of other pixels, and the like.

As a specific constitution, as depicted in FIG. 6, the control computer 20 comprises the CPU 21; further, a main storage unit, which is controlled by the CPU 21, comprises a ROM 22, a RAM 23, and a CF 25. The CF 25 stores: a threshold value file 25a that stores a density threshold value (discussed later); an inspection result log file 25b that stores the inspection image, the inspection result, and the like; etc.

Furthermore, the control computer 20 comprises: a display control circuit, which controls the display of data on the monitor 26; a key input circuit, which captures the key input data from the touch panel of the monitor 26; an I/O circuit board, which controls the printing of data on a printer (not shown) and the like; a USB 24 that serves as an external connection terminal; and the like.

Furthermore, the CPU 21, the ROM 22, the RAM 23, the CF 25, and the like are mutually connected via bus lines, such as an address bus and a data bus.

In addition, the control computer 20 is connected to the conveyor motor 12f, a rotary encoder 12g, the X-ray irradiating device 13, the X-ray line sensor 14, a photoelectric sensor 15, and the like.

The rotary encoder 12g is mounted to the conveyor motor 12f and operates by detecting the transport speed of the conveyor 12 and transmitting such to the control computer 20.

The photoelectric sensor 15 is a synchronization sensor for detecting the timing at which the product G, which is the product to be inspected, comes to the position of the X-ray line sensor 14, and comprises a pair of a light projecting device and a light receiving device, which are disposed so that they sandwich the conveyor.

Determination of a Defective Product by the Control Computer X-ray Image Generator When the control computer 20 receives a signal from the photoelectric sensor 15 and the product G passes through the fan shaped X-ray irradiating unit (refer to the diagonally lined portions depicted in FIG. 3 and FIG. 5A), the X-ray line sensor 14 acquires the radioscopic image signals (refer to FIG. 7) in a short time interval and generates an X-ray image of the product G based on these radioscopic image signals. Namely, the time data is acquired from each of the pixels 14a of the X-ray line sensor 14 in a short time interval, and a two-dimensional image is generated from these data.

Foreign Matter Contamination Inspection

A foreign matter inspection routine, which is executed by the CPU 21 of the control computer 20, performs image processing of the X-ray image acquired as described above, and then determines whether the product is nondefective or defective (whether it is contaminated with foreign matter) via a plurality of determination systems. Examples of determination systems include, for example, a trace detection system, a binarized detection system, and a masked binarized detection system. If even one of the results from these determination systems is defective (image of foreign matter depicted in FIG. 7), then that product G is determined to be a defective product.

The trace detection system and the binarized detection system make their determinations on the area wherein the image is not masked. On the other hand, the masked binarized system makes its determination on the area wherein the image is masked. The mask is set with respect to the product G container portion and the like.

With the trace detection system, a reference level (threshold value) is set in accordance with the approximate thickness of the product to be detected, and the product G is determined to be contaminated with foreign matter if the image darkens greater than that reference level. With this system, it is possible to detect defective products by detecting a comparatively small amount of foreign matter.

Determination of a Conveyor Mount Failure by the X-ray Inspection Apparatus

With the X-ray inspection apparatus 10 according to the present embodiment, before starting the inspection of products for foreign matter contamination, an inspection is performed to determine whether the mounting of the conveyor 12 has been neglected, whether the conveyor 12 is mismounted, and the like in order to prevent the leakage of X-rays to the outside of the apparatus due to such causes. Furthermore, if a neglected mounting of the conveyor 12 and the like has been detected, then the control computer 20 will control the X-ray irradiating device 13 so as to prohibit the irradiation of X-rays.

Namely, as depicted in FIG. 5A, if the conveyor 12 is mounted at the normal position inside the shield box 11, then the amount of X-rays detected at the four to five pixels at each end of the X-ray line sensor 14 is comparatively less than at other pixels 14a. This state (the position and number of pixels on each end) is set as the reference state for the normal mounting of the conveyor 12 and is stored in the storage unit, such as the RAM 23 discussed above. Furthermore, the reference state (the position and number of pixels wherein the amount of X-rays detected decreases) stored in the storage unit, such as the RAM 23, should be associated with the shield units of the conveyor 12 and newly stored every time the conveyor 12 (conveyor frame 12b) is replaced.

Furthermore, as depicted in FIG. 5B, if the mounting of a conveyor 12 that was removed from inside the shield box 11 for cleaning and the like is neglected, then X-rays are detected at all pixels 14a of the X-ray line sensor 14. Consequently, the level of X-rays detected at prescribed pixels 14a (several pixels on each end of the X-ray line sensor 14) compared with the reference state stored in the storage unit, such as the RAM 23, is the same as at other pixels 14a, and the control computer 20 determines that there is a mount error of the conveyor 12. Furthermore, the irradiation of X-rays from the X-ray irradiating device 13 is prohibited and an indication to the effect that there is a mount failure of the conveyor 12 is displayed on the monitor 26.

In addition, if the conveyor 12 shifts and is not mounted at the normal position, then it is possible to determine that there is a mount failure of the conveyor 12 based on the detection of X-rays at the prescribed several pixels on each end of the X-ray line sensor 14. For example, it is expected that the amount of X-rays detected will decrease at the same number of pixels on each end of the X-ray line sensor 14; however, if the pixels 14a at which the amount of X-rays detected is decreased are in a left-right asymmetric state, such as eight pixels on one side and two pixels on the other side, then it is determined that there is a mount failure of the conveyor 12.

Furthermore, during the inspection for a mount failure of the conveyor 12, which is performed before starting the inspection for foreign matter contamination, the amount of X-rays irradiated from the X-ray irradiating device 13 may be reduced more than during the normal inspection (e.g., approximately 30 KV at 1 mA). Thereby, even if a mount failure of the conveyor 12 occurs, it is possible to suppress the amount of X-rays that leak to the outside of the apparatus to less than approximately 1 μSv/h when inspecting the conveyor 12 for a mount failure.

However, if a mount failure of the conveyor 12 is not detected, then the amount of X-rays irradiated from the X-ray irradiating device 13 is increased to the amount when performing a normal inspection, and the inspection for foreign matter contamination is started while transporting the product G by the conveyor 12.

Features of the X-ray Inspection Apparatus (1)

With the X-ray inspection apparatus 10 according to the present embodiment, the shield units 12d, which each block a portion of the amount of X-rays irradiated from the X-ray irradiating device 13, are provided to the conveyor 12 (conveyor frame 12b). Furthermore, these shield units 12d are constituted so that the X-rays detected by some of the pixels 14a, which constitute the X-ray line sensor 14, are less than that at other pixels 14a. Furthermore, the control computer 20 stores the position, number, and the like of the pixels 14a in which the amount of X-rays detected is reduced when the conveyor 12 is properly mounted, and, before starting the inspection for foreign matter contamination, determines whether there is a mount failure of the conveyor 12 by irradiating a small amount of X-rays and detecting whether X-rays are detected at the pixels 14a that were stored as mentioned above.

Thereby, by simply verifying the signals of the pixels 14a of the X-ray line sensor 14 wherein the X-rays are blocked by the shield units 12d, which are integrated with the conveyor 12, i.e., by simply verifying the signals of the pixels wherein the amount of X-rays detected is less than that at other pixels, it is possible to determine beforehand whether there is a mount failure of the conveyor 12 before starting the inspection for foreign matter contamination. Consequently, even without separately providing a member, such as a switch, that detects whether the conveyor 12 is mounted, it is possible to prevent the leakage of X-rays due to a mount failure of the conveyor 12 with a simple constitution by just forming the opening 12c, which is conventionally formed in the conveyor frame 12b, and by forming shield units 12d integrally with the conveyor 12 by devising a positional relationship between the opening 12c and the X-ray line sensor 14.

(2)

With the X-ray inspection apparatus 10 according to the present embodiment, the control computer 20 prohibits the irradiation of X-rays from the X-ray irradiating device 13 if it is determined that there is a mount failure of the conveyor 12 by the method of detecting a mount failure of the conveyor 12 discussed above.

Thereby, it is possible to prevent the leakage of X-rays to the outside of the apparatus by inspecting the products for foreign matter contamination while irradiating X-rays in an unmounted state or a mismounted state (mount failure state) of the conveyor 12.

(3)

The X-ray inspection apparatus 10 according to the present embodiment comprises a storing means, such as the RAM 23, as the storage unit that stores the state (the position, number, and the like of pixels wherein the amount of X-rays detected is reduced) that constitutes the reference for the mount failure inspection of the conveyor 12.

Thereby, it is possible to easily determine whether there is a mount failure of the conveyor 12 just by determining whether there is a match with the reference state stored in the storage unit, such as the RAM 23.

(4)

With the X-ray inspection apparatus 10 according to the present embodiment, the shield units 12d, which function as X-ray shield units, are formed integrally with the conveyor frame 12b and as portions thereof.

Thereby, because the shield units 12d are integral with the conveyor 12 from the start, it is possible to further simplify the constitution compared with the case wherein members that serve as the X-ray shield units are separately formed and fixed to the conveyor 12.

(5)

With the X-ray inspection apparatus 10 according to the present embodiment, the conveyor 12, which has an endless conveyor belt 12a, a conveyor frame 12b, a conveyor motor 12f, and the like, is used as a transport unit that transports the products.

Thereby, it is possible to easily form the X-ray shield units, which are integral with the conveyor 12, in the conveyor frame 12b by forming an opening, a slit, and the like therein.

(6)

With the X-ray inspection apparatus 10 according to the present embodiment, portions of the conveyor frame 12b surrounding the opening 12c, which is formed in the conveyor frame 12b, are used as the X-ray shield units (the shield units 12d).

Thereby, it is possible to easily detect whether there is a mount failure of the conveyor 12 by disposing the X-ray line sensor 14 at a position below where the X-rays are blocked by the shield units 12d.

(7)

With the X-ray inspection apparatus 10 according to the present embodiment, the X-ray line sensor 14, which comprises the plurality of pixels 14a, is used as a light receiving unit that detects the X-rays irradiated from the X-ray irradiating device 13.

Thereby, by disposing the X-ray line sensor 14 so that it is long in a direction orthogonal to the transport direction, it is possible to make it so that the X-rays at both ends of the X-ray line sensor 14 are blocked by the shield units 12d. Thereby, it is possible to easily determine whether there is a mount failure of the conveyor 12 based on whether the amount of X-rays detected at prescribed pixels 14a on each end of the X-ray line sensor 14 is reduced.

(8)

With the X-ray inspection apparatus 10 according to the present embodiment, the shield units 12d block the X-rays detected at a number of pixels 14a on each side of the X-ray line sensor 14, which is disposed below and along the opening 12c formed in the conveyor frame 12b.

Thereby, it is possible to determine whether there is a mount failure of the conveyor 12 based on whether the amount of X-rays detected at several pixels 14a on each end of the X-ray line sensor 14 is less than that of other pixels 14a.

Other Embodiments

An embodiment of the present invention was described above, but the specific constitution is not limited to this embodiment, and it is understood that variations and modifications may be effected without departing from the spirit and scope of the invention.

(A)

The abovementioned embodiment was explained by citing an example of a case wherein an opening 12c is formed in the conveyor frame 12b, and portions thereof on each end of the opening 12c are used as X-ray shield units (shield units 12d) as depicted in FIG. 3. However, the present invention is not limited thereto.

Figure 8:
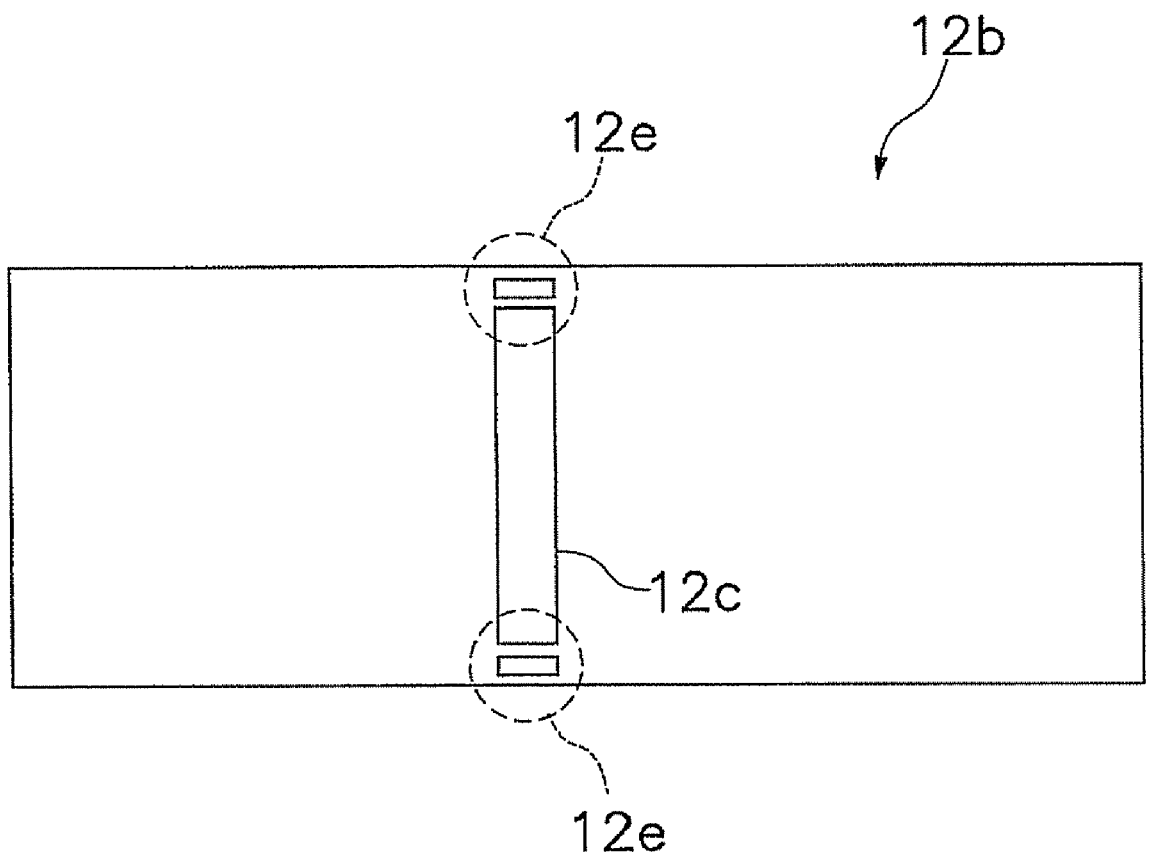
FIG. 8 is a plan view that depicts the conveyor frame mounted inside the X-ray inspection apparatus according to another embodiment of the present invention.
Figure 9A:
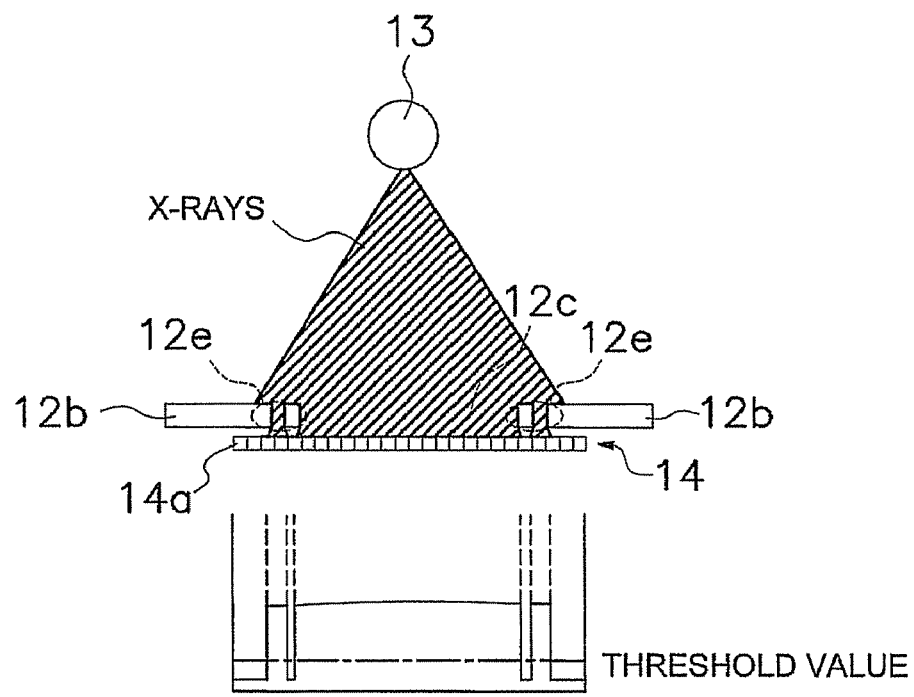
FIG. 9A depicts the X-ray irradiation state of the conveyor frame depicted in FIG. 8 and a graph of the amount of X-rays detected by the line sensor at that time.

For example, as depicted in FIG. 8 and FIG. 9A, a slit 12e may be formed in the conveyor frame 12b in the vicinity of each end of the opening 12c in a direction orthogonal to the transport direction, and the portions of the conveyor frame 12b wherein these slits 12e are formed may be used as the X-ray shield units. In this case, the same effect as in the abovementioned embodiment can be obtained, and it is possible to determine whether the conveyor 12 is mounted at the portions of the conveyor frame 12b wherein the slits 12e are formed; consequently, it is possible to inspect the conveyor 12 for a mount failure in a state wherein it is clearer that what is blocking the X-rays is definitely the portions (shield units) of the conveyor frame 12b.

Figure 9B:
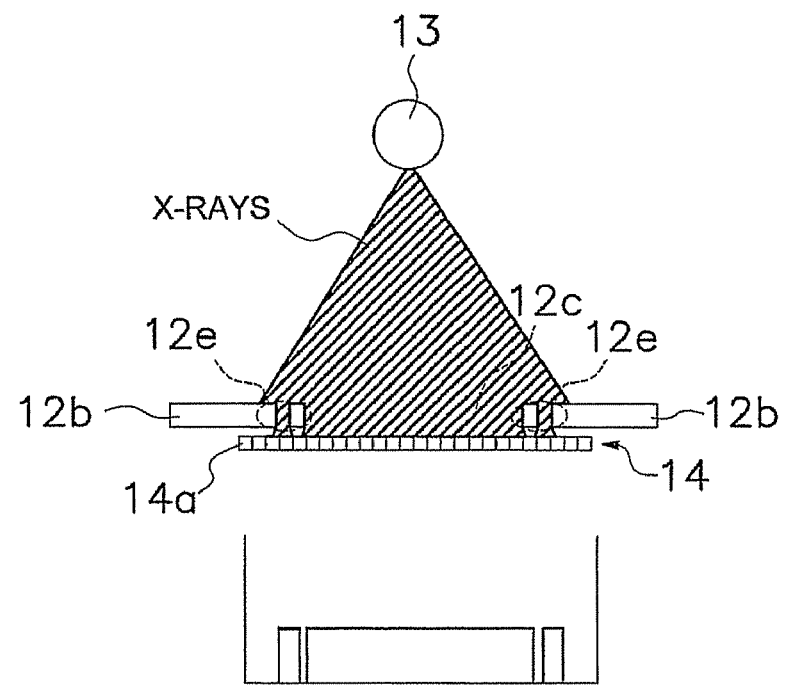
FIG. 9B graphs the amount of X-rays detected in FIG. 5A in binary form.

In addition, the presence of a mount failure of the conveyor 12 may be determined by setting a threshold value for the amount of X-rays detected at the X-ray line sensor 14 as depicted in FIG. 9A, converting the detection result depicted in FIG. 9A to binary form based on the threshold value, and generating a graph as depicted in FIG. 9B. In this case, it is possible to inspect the conveyor 12 for a mount failure by checking the High-Low pattern of the binarized signal in order to verify the signals of the pixels 14a of the X-ray line sensor 14 blocked by portions (shield units) of the conveyor frame 12b.

(B)

The abovementioned embodiment was explained by citing as an example a case wherein the shield units 12d, which were formed using the opening 12c and the like formed in the conveyor frame 12b, were used as the X-ray shield units. However, the present invention is not limited thereto.

For example, even if not using an opening, a slit, and the like directly formed in the conveyor frame 12b, members that block portions of the X-rays may be separately formed and then integrally fixed to the conveyor 12. Even in this case, it is possible to detect the presence of a mount error of the conveyor 12 because the members that serve as the X-ray shield units also move attendant with the movement of the conveyor 12.

(C)

The abovementioned embodiment was explained by citing as an example a case wherein the shield units 12*d* are formed so that they block the X-rays detected at four to five pixels 14*a* from each end of the X-ray line sensor 14. However, the present invention is not limited thereto.

For example, the present invention may be constituted so that the X-rays at just a few pixels 14*a* at one end of the X-ray line sensor 14 are blocked by the shield units 12*d*, or so that the number of pixels at which the X-rays are blocked by the shield units 12*d* differs for each end of the X-ray line sensor 14.

Specifically, the present invention may be constituted so that the X-rays are blocked by the shield units 12*d* at five pixels from one end of the X-ray line sensor 14, or may be constituted so that the X-rays are blocked by the shield units 12*d* at eight pixels from one end and three pixels from the other end.

Even in this case, the same effect as described above is achieved by storing in the storage unit, such as the RAM 23, the pixels 14*a* (the reference state) wherein the X-rays are blocked by the shield units 12*d* when the conveyor 12 is mounted at the normal position.

(D)

The abovementioned embodiment was explained by citing as an example a case wherein the opening 12*c* that forms the shield units 12*d* is formed as a quadrilateral opening. However, the shape and size of the opening 12*c* in the present invention is not limited to the constitution described in the abovementioned embodiment.

(E)

The abovementioned embodiment was explained by citing as an example a case of performing an inspection by irradiating a product with X-rays. However, the present invention is not limited thereto.

For example, other than X-rays, it is possible to perform the inspections by irradiating other types of radiation, such as β rays, γ rays, electromagnetic waves, and the like.

INDUSTRIAL FIELD OF USE

Because the X-ray inspection apparatus of the present invention achieves an effect wherein it is possible with a simple constitution to verify whether a transport unit is properly mounted, it is possible to widely adapt the present invention to radiographic inspection apparatuses that comprise a transport unit that transports products to be inspected and that uses radiation, such as X-rays.

The invention claimed is:

1. An X-ray inspection apparatus configured to inspect a product, which is being transported, by irradiating the product with X-rays and detecting the X-rays that pass through the product, comprising:

an irradiation unit configured to irradiate the product with X-rays;

a light receiving unit configured to detect the X-rays irradiated from the irradiation unit;

a transport unit, which is disposed between the irradiation unit and the light receiving unit, configured to transport the product;

an X-ray shield unit that is integral with the transport unit and is formed in an area irradiated by the X-rays;

a control unit configured to detect the position at which the X-rays are blocked by the X-ray shield unit based on the amount of X-rays detected at the light receiving unit, and determine whether the transport unit is properly mounted based on the position; and a storage unit configured to store the position of the light receiving unit at which the X-rays are blocked by the X-ray shield unit when the transport unit is properly mounted.

2. An X-ray inspection apparatus as recited in claim 1, wherein the control unit is configured to prohibit the irradiation of X-rays from the irradiation unit if it is determined that the transport unit is not properly mounted.

3. An X-ray inspection apparatus as recited in claim 1, wherein the X-ray shield unit is formed integrally with a frame that comprises the transport unit.

4. An X-ray inspection apparatus as recited in claim 1, wherein the transport unit is a transport conveyor that comprises:

an endless transport belt configured to transports the product;

a drive mechanism configured to rotate the transport belt; and a frame disposed on the inner side of the transport belt.

5. An X-ray inspection apparatus as recited in claim 4, wherein the X-ray shield unit is a portion of the frame comprising the transport conveyor in which a slit is formed.

6. An X-ray inspection apparatus as recited in claim 4, wherein the X-ray shield unit is a portion of the frame comprising the transport conveyor in which an opening is formed.

7. An X-ray inspection apparatus as recited in claim 1, wherein the light receiving unit is a line sensor.

8. An X-ray inspection apparatus as recited in claim 7, wherein the X-ray shield unit is disposed at a position wherein the X-rays detected at one end or both ends of the line sensor are blocked.

\* \* \* \* \*